United States Patent [19]

Brown

[11] 4,022,058
[45] May 10, 1977

[54] APPARATUS FOR DETERMINING THE ARRIVAL TIME OF ALTERNATING SIGNALS

[76] Inventor: Alvin E. Brown, 2865 N. Mountain Ave., Claremont, Calif. 91711

[22] Filed: Aug. 7, 1975

[21] Appl. No.: 602,918

[52] U.S. Cl. .................................. 73/194 A; 73/560
[51] Int. Cl.² ............................................. G01F 1/66
[58] Field of Search ............. 73/194 A, 67.5 R, 560

[56] References Cited

UNITED STATES PATENTS

| | | | |
|---|---|---|---|
| 3,720,105 | 3/1973 | Cirulis | 73/194 A |
| 3,751,979 | 8/1973 | Ims | 73/194 A |
| 3,780,577 | 12/1973 | Brown | 73/194 A |
| 3,818,757 | 6/1974 | Brown | 73/194 A |

*Primary Examiner*—Charles A. Ruehl

[57] ABSTRACT

Received ultrasonic bursts of energy are rectified and converted into pulse trains and also envelope detected. The envelope is fed to a ramp generator whose output is threshold detected to provide an arrival delay signal corresponding in time to the peak amplitude of the received bursts. A regulator circuit varies the timing of the arrival delay signal to coincide with the next negative-going zero crossover of the pulse train. A timing generator provides a reference delay offset, relative to the transmission time of the ultrasonic bursts, by the expected transit time thereof. The timing of the reference signal is varied in the same manner as the arrival delay signal by the regulator circuit and compared with the positive-going zero-crossover in the pulse train next following the negative-going zero-crossover. This determines accurately the actual time of arrival of the bursts, using low components.

15 Claims, 4 Drawing Figures

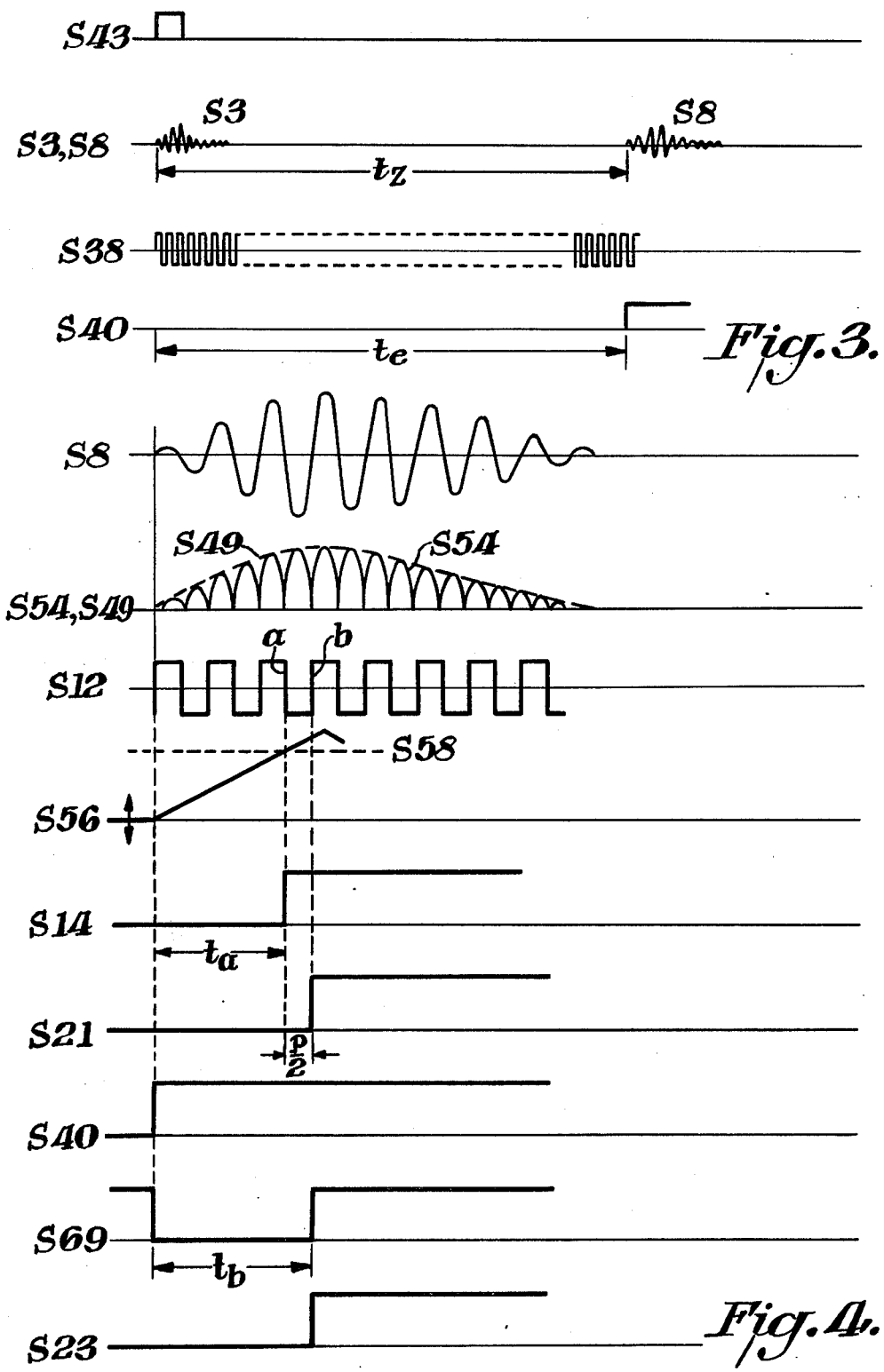

APPARATUS FOR DETERMINING THE ARRIVAL TIME OF ALTERNATING SIGNALS

CROSS REFERENCE TO RELATED APPLICATIONS

This application describes a portion of the system described in an application Ser. No. 603,294 filed Aug. 4, 1974 and entitled Apparatus For The Ultrasonic Measurement Of The Flow Velocity of Fluent Media.

BACKGROUND OF THE INVENTION

This invention relates to apparatus for determining the arrival time of alternating signals and, more particularly, to apparatus for determining the arrival time of an ultrasonic signal.

From German Pat. No. 2,322,749 and U.S. Pat. No. 3,780,577 devices are known for the ultrasonic measurement of the flow velocity of fluent media and the sonic velocity in fluent media, in which ultrasonic signals are alternately transmitted upstream and downstream along a measuring path which is provided with two ultrasonic transducers and has at least one component extending in the flow direction. At the instant of transmission, the transducer on the transmission side is momentarily energized and a time generator is simultaneously actuated which delivers a reference signal after the expected transit time. The time generator may include a voltage-controlled oscillator which is operated at a frequency $f_1$ during downstream measurement and with a frequency $f_2$ during upstream measurement. A series-connected counter counts a predetermined number of output impulses after the instant of transmission. If the expected transit time is shorter than the actual transit time, the frequency of the oscillator is reduced by means of a regulating circuit; if the expected transit time is longer than the actual transit time, the frequency of the oscillator is increased by means of the regulating circuit. By reason of this adaptation, the oscillator frequencies correspond to the reciprocal values of the downstream and upstream transit times and can be evaluated to obtain the flow velocity and the sonic velocity. If the transducer on the transmission side in such an apparatus is energized at the instant of transmission, it will not immediately emit the high frequency ultrasonic signal, which may for example have a frequency of 1 MHz, at maximum amplitude; the amplitude rather increases gradually. As a result, the end of the transit time, that is to say the commencement of the ultrasonic signal on the receiver side, can only be determined by the fact that the transducer on the receiver side receives an ultrasonic oscillation which is only little different from zero. This does not permit accurate measurement. In the known cases, therefore, the actual instant of comparison has been delayed with reference to the commencement of the signal. This occurs on the receiver side with the aid of arrival delay means by which the received ultrasonic signal is rectified, at least the first portion of the envelope of the rectified ultrasonic signal is converted to a substantially linear rising signal, and the latter is fed to a threshold value detector which, on reaching the threshold value, delivers an arrival delay signal that is delayed relatively to the actual arrival. In a second channel the received ultrasonic signal is amplified and clipped so that a rectangular signal of the same phase is obtained. The zero crossover of this rectangular signal with rising or positive-going leading edge following the arrival delay signal is utilized as a corrected arrival signal. Simultaneously, in the reference delay means a reference delay time was added at the instant of the actual reference signal, the reference delay time being constant, as is the arrival delay time, but somewhat larger than same. At the end of this reference delay time a time comparison signal is delivered as a corrected reference signal which is compared with the aforementioned zero crossover. It is immaterial whether on the receiver side the commencement of the arriving ultrasonic signal is determined very accurately. This is because a slightly retarded determination of the commencement of the signal merely displaces the arrival delay time and thus the arrival delay signal but not the selected zero crossover that is used for the measurement. This results in a very high measuring accuracy.

However, difficulties arise when the commencement of the arriving ultrasonic signal is determined so late that the arrival delay signal appears immediately prior to the selected zero crossover. In that case it can happen that the next zero crossover is instead used for the measurement and the measuring result is in error. One was therefore compelled to use very accurately operating components on the receiver side for permitting determimation of commencement of the signal as rapidly as possible, preferably still within the first half period.

The invention is based on the object of providing an improved apparatus of the aforementioned kind in which accurate determination of the commencement time is possible without placing such high requirements as hitherto on the accurate determination of the commencement of the arriving ultrasonic signal.

SUMMARY OF THE INVENTION

This object if fulfilled in accordance with the invention by a phase detector which determines the phase position of the arrival delay signal with reference to a zero crossover of the trailing edge of one of the pulses in a pulse train derived from the received signal, and by regulating means which act on the arrival delay means and, in dependence on the phase position, change the arrival delay time in the sense of displacing the arrival delay signal towards the last-mentioned zero crossover.

In this construction, the arrival delay time is no longer constant but variable. By a regulating circuit it is passed after the zero crossover of the pulse train which precedes the zero crossover to be selected by half a period. This ensures on the one hand that the arrival delay signal appears in sufficient time to enable the next zero crossover that serves for the measurement to be selected with certainty and on the other hand that late determination of commencement of the signal is permissible within wider limits than hitherto because the arrival delay time is automatically shortened correspondingly. This also permits one to use simpler readily available circuit elements because the regulating circuit compensates the errors caused thereby.

It is also advantageous if the regulating means also act on the reference delay means and change the reference delay time in the same sense as the arrival delay time. This enables further corrections to be made automatically without the need for recalibrating the instrument and insures the reference delay time coincides with the leading edge of the next positive-going signal following the zero crossing.

In an apparatus wherein in the arrival delay means the received ultrasonic signal is rectified, at least the first portion of the envelope of the rectified ultrasonic signal is transformed to a substantially linear rising signal and the latter is fed to a threshold detector which causes the arrival delay signal to be emitted when the threshold value is reached, it is preferred that the phase detector delivery early signals when the arrival delay signal arrives too early and late signals when it arrives too late, that the early signals of one sign and the late signals of opposite sign can be fed to an integrator, and that a control voltage derivable at the output of the integrator serves to change the arrival delay time. When the phase position of the arrival delay signal coincides accurately with the zero crossover of the other polarity, early and late signals occur alternately so that the integrator delivers a constant control voltage. If the early signals or the late signals predominate, the control voltage decreases or rises, respectively.

In particular, the phase detector can comprise a D-flip-flop of which the preparatory or data input has the pulse train fed to it, the stage or clock input has the arrival delay signal fed to it, one output delivers the early signals and the other output delivers the late signals.

It is of particular advantage if the control voltage is feedable to the one input and the envelope to the other input of a differential amplifier producing the linear rising signal. If the difference between the control voltage and the envelope increases, the threshold value is reached earlier and if the difference decreases the threshold value is reached later. The control voltage could instead exert influence in a different manner, for example by altering the threshold value itself.

In a preferred embodiment the reference delay means include a monostable multi-vibrator which is triggered by the reference signal and which comprises and RC element determining the trigger period, the condenser charging voltage of the RC element being governed by the control voltage, and also include a flip-flop which is resettable after each measurement and which is set by the multi-vibrator at the end of each trigger period and then delivers the time comparison signal. The leading edge of the time comparison signal serves for the accurate determination of the end of the reference delay time. It is a permanent binary signal which terminates only on resetting.

Further, on reaching the threshold value, the threshold generator may deliver a threshold signal which sets a flip-flop that is resettable after each measurement and delivers the arrival delay signal. The arrival delay signal is therefore also a permanent binary signal which terminates only upon resetting the flip-flop and the leading edge of which accurately indicates the end of the arrival delay time.

The zero passage selector means preferably comprise a D-flip-flop which is resettable after each measurement, has the arrival delay signal fed to its preparatory input and the rectangular signal to its stage input and delivers the zero passage signal at one output. The zero passage signal is therefore a permanent binary signal which terminates on resetting the flip-flop and the leading edge of which accurately gives the instant of the zero passage.

In an advantageous embodiment, the arrival time detector comprises a D-flip-flop which has the time comparison signal fed to its preparatory input and the zero passage signal fed to its stage input, and delivers an early measured signal at its one output and a late measured signal at its other output depending on whether the zero crossover signal occurs before or after the time comparison signal. The early or late measured signals can than be evaluated in the usual way for measuring and indicating purposes, for example to adapt the frequency of the time generator oscillator to the actual transit time.

Further, indicating means may be provided comprising two incandescent diodes each energized by an inverter controlled by the early or late signals, respectively. On correct functioning of the regulating circuit, these incandescent diodes should light up alternately.

BRIEF DESCRIPTION OF THE DRAWINGS

The invention will now be described in more detail with reference to the example shown in the drawing, wherein:

FIG. 3 shows the time course of the transmission signal, ultrasonic signals, counting signals and reference signal, and FIG. 4 shows the time course of various signals occurring in the apparatus.

Figure 1:
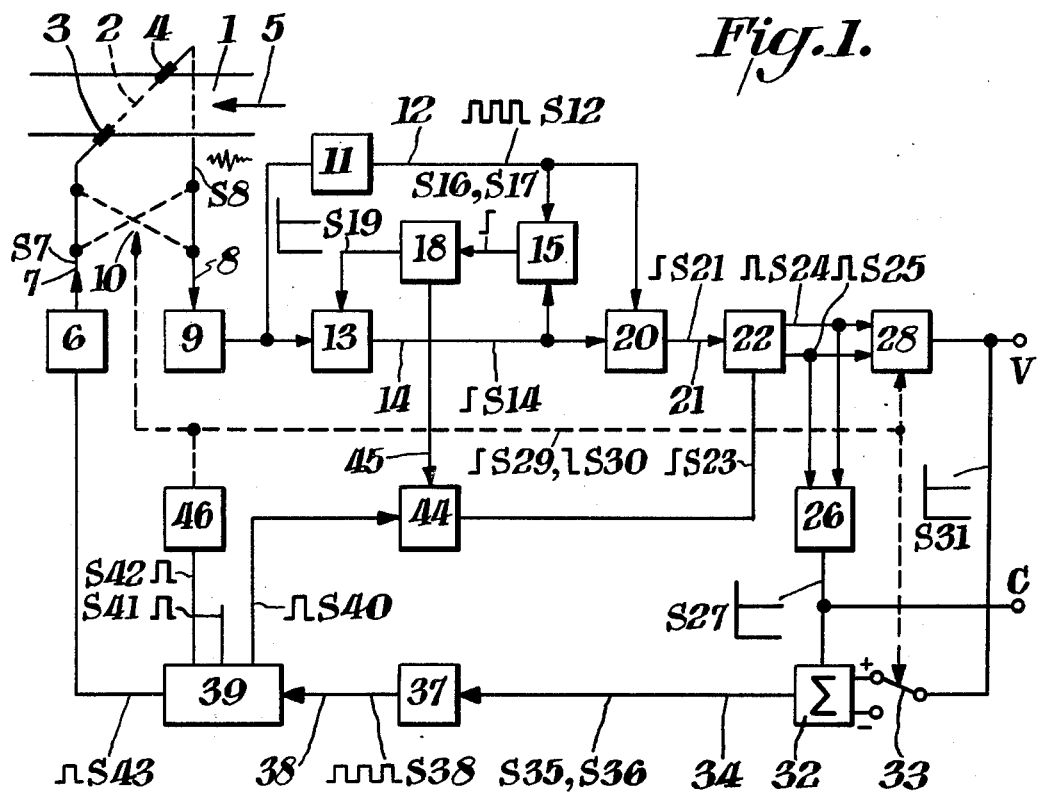
FIG. 1 is a block circuit diagram of an ultrasonic measuring apparatus comprising the apparatus according to the invention.

According to FIG. 1, a channel 1 contains an ultrasonic measuring path 2 which is limited by two ultrasonic transducers 3 and 4 and disposed obliquely to the flow direction 5 of the medium flowing through the channel 1. Transmission means 6 deliver an energizing signal S7 to the transducer 3 through the line 7, the transducers thereupon delivering an ultrasonic signal at the transducer's resonant frequency, for example 1 MHz through the medium in the channel 1. At the end of the transit time, this signal is received by the transducer 4 and converted to an electric ultrasonic signal S8 which is fed through a line 8 to receiver means 9. The lines 7 and 8 are interchangeable by a switch 10 so that the transducers 3 and 4 can alternately serve as ultrasonic transmitter and as ultrasonic receiver. In the receiving means the ultrasonic signal S8 is amplified and the processed further in two channels.

The first channel comprises an amplifier 11, in the output line 12 of which there occurs a rectangular signal or pulse train S12 having the frequency of the ultrasonic signal S8. In the second channel there are arrival delay means 13, at the output 14 of which an arrival delay signal S14 occurs at the end of an arrival delay time. In a phase detector 15 the arrival delay signal S14 is compared with the adjoining trailing edge of an impulse of the rectangular signal S12. The phase detector emits early signals S16 or late signals S17 depending on whether the arrival delay signal S14 occurred earlier or later than the trailing edge of the impulse of the rectangular signal S12. Regulating means 18 are controlled in dependence on this, the regulating means delivering an output signal S19 to the arrival delay means 13 so that the arrival delay time is shortened or extended until the arrival delay signal S14 accurately coincides with the trailing edge. This determines a defined zero passage with the trailing edge of the rectangular signal S12.

The arrival delay signal S14 is further fed to zero passage selector means 20 which are also fed by the rectangular signal S12. A zero crossover signal S21 occurs at the output 21 when the first rising flank or leading edge of the rectangular signal S12 appears after occurrence of the arrival delay signal S14. This determines a defined zero passage.

The zero passage signal S21 is compared with a time comparison signal S23 in an arrival time detector 22. An early measured signal S24 is emitted if the zero passage signal S21 occurs earlier than the time comparison signal S23 and a late measured signal S25 is emitted if it occurs later. As will be evident from the Applicants' copending application "Apparatus for the ultrasonic measurement of the flow velocity of fluent media", integration of all early measured signals of one sign and all late measured signals of the opposite sign in a voltage level generator 26 can give a main signal S27 which is a direct measurement for the sonic velocity $c$. In a second signal level generator 28 the early and late measured signals are evaluated with regard to the upstream signals S29 and downstream signals S30 which indicate the transmission direction. By integrating all downstream early measured signals of one sign and all upstream early measured signals of the opposite sign, an auxiliary signal S31 is obtained which is a measurement for the flow velocity $v$. The late measured signals or the early and late measured signals can be processed in a similar manner.

The main signal S27 is fed directly to a summing circuit 32 but the auxiliary signal S31 is fed with alternately positive and negative sign through a switch 33 which is dependent on the transmission direction. Consequently control signals S35 and S36 occur alternately at the output of the summing circuit, the control signals influencing a voltage-controlled oscillator 37 in such a way that it delivers at its output 38 trains of impulses S38 with a frequency $f_1$ on downstream measurement and a lower frequency $f_2$ on upstream measurement. These trains of impulses are fed to a counter 39 which, after counting 256 impulses by way of example, delivers a reference signal S40, a resetting signal S41 a little later, then a transmission direction changing signal S42 and, simultaneously with commencement of counting, a transmission signal S43 to the transmission means 6. The reference signal S40 is fed to reference delay means 44 in which, on arrival of the reference signal S40, a reference delay time is started; at the end of the reference delay time the time comparison signal S23 is emitted. In addition, the control signal S19 is fed through the input 45 and with the aid of this the reference delay time is variable. The transmission direction changing signal S42 is fed to a direction generator 46 which switches over the switches 10 and 33 and feeds the corresponding downstream and upstream signals to the signal level generator 28.

Figure 2:
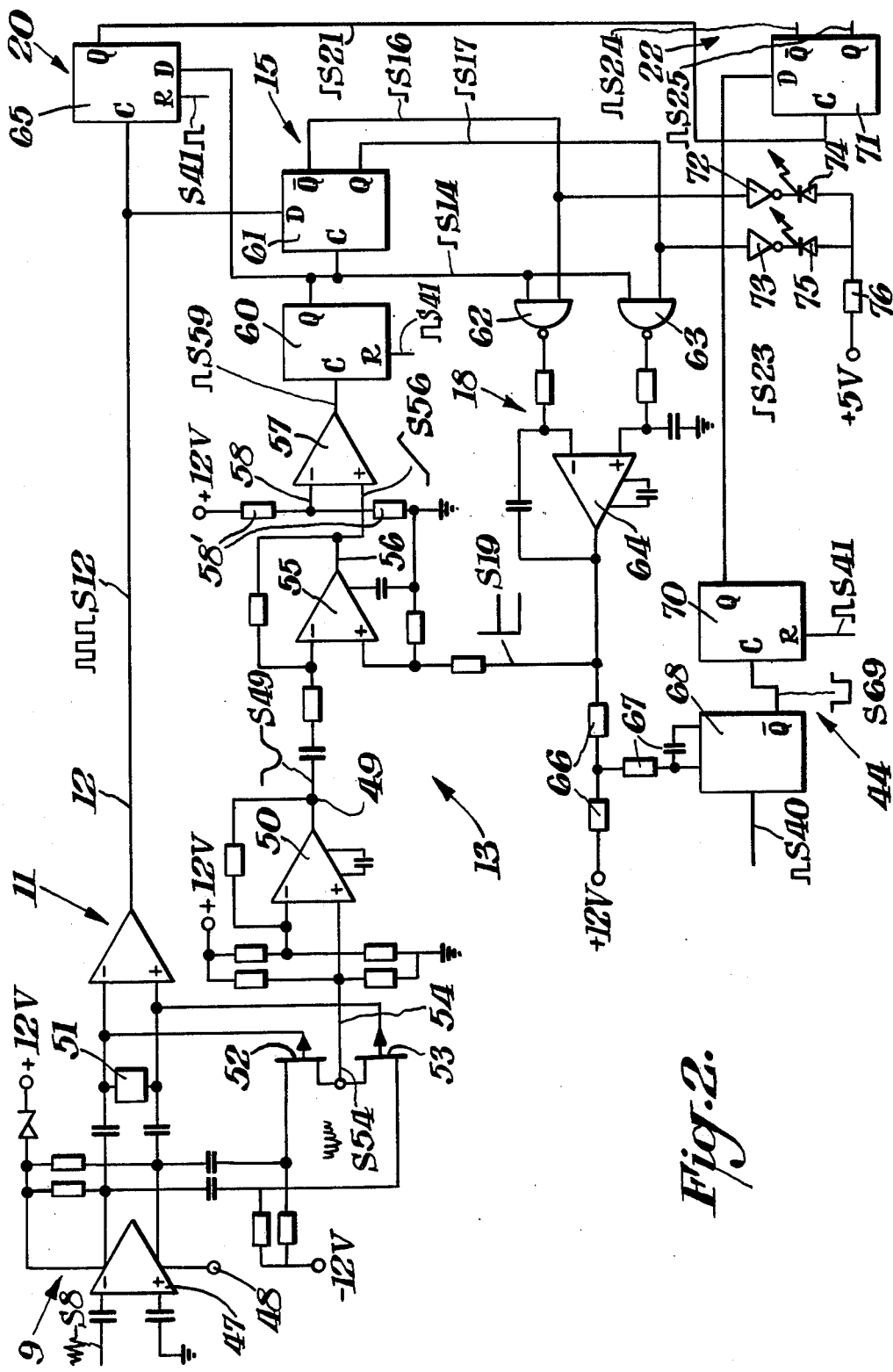
FIG. 2 is a simplified representation of the circuit of one embodiment of the apparatus.

FIG. 2 shows an embodiment for the equipment 9, 11, 13, 15, 18, 20, 22 and 44 of FIG. 1. The receiver means 9 comprises in the final stage an amplifier 47 of which the inverting input has the electric ultrasonic signal S8 fed to it. In this amplifier, the gain can be regulated. By means of a circuit (not shown), regulation is effected by applying a regulating voltage to a terminal 48 in such a way that the amplitude of an envelope curve signal S49 occurring at the output 49 of an amplifier 50 remains constant. The output of this amplifier 47 can have interfering frequencies, which do not correspond to the ultrasonic frequency, removed from it by an LC filter circuit 51. The signal values thus obtained are so amplified and clipped in the amplifier 11 that the rectangular signal S12 appears in the line 12. The amplified ultrasonic signal is additionally fed to two field effect transistors 52 and 53 for the purpose of full wave rectification so that a rectified ultrasonic signal S54 appears at their output 54. This rectified signal is smoothed in the amplifier 50, which serves as low-pass filter, so that the envelope curve S49 appears at the output 59.

The envelope S49 is fed to a differentiator 55 (which in a preferred embodiment may be a ramp amplifier whose slew rate is limited). The differentiator delivers a signal S56 at its output 56 with a constant slope determined by the slew rate of ramp amplifier as long as the rise time of the input envelope S49 exceeds the slew rate of the amplifier. This output signal S56 is compared in a threshold value detector 57 with a fixed threshold value supplied through the input 58 by a voltage divider 58'. On reaching this threshold value, a signal S59 is applied to the clock input C of a D-flip-flop 60 which is set to emit the arrival delay signal S14 at its output Q until resetting is effected by the resetting signal S41.

The arrival delay signal S14 is fed to the stage or clock input of a D-flip-flop 61, of which the preparatory input D is fed with the rectangular signal S12. Consequently, early signal S16 appears at the output $\overline{Q}$ or late signal S17 at the output Q, which are gated with the arrival delay signal S14 in NAND elements 62 or 63 and therefore can be fed to an integrator 64 as impulses of substantially constant charge. The early signals are fed to the inverting and the late signals to the non-inverting input of the integrator 64. If the arrival delay signal S14 does not accurately coincide with the trailing edge of an impulse of the rectangular signal S12, the number of early or late signals predominates and the size of the control voltage S19 changes at the output of the integrator 64. This output voltage is fed to the non-inverting input of the ramp amplifier 55, as a result of which the output voltage S56 is displaced upwardly or downwardly parallel to itself. This changes the point of intersection with the threshold value and thus the instant of the threshold value signal S59 and of the arrival delay signal S14 until the last-mentioned signal again coincides with the falling flank of the rectangular signal S12.

The thus regulated arrival delay signal S14 is fed to the preparatory input D of the D-flip-flop 65 serving as zero crossover selector means to the stage input C of which the rectangular signal S12 is fed. Consequently, during the next zero crossover, i.e. at the leading edge of the next impulse in the rectangular signal S12, the zero crossover signal S21 occurs at the output Q and remains until the output condition of the flip-flop 65 is reset by the resetting signal S41.

The control voltage S19 acts through a voltage divider 66 on an RC element 67 of a monostable multivibrator 68 which is triggered by the reference signal S40 and, after a period determined by the RC element 67, returns to its original state. During the triggered period, which also serves as a reference delay time, a signal S69 occurs at the output $\overline{Q}$ of the multi-vibrator 68. This signal is fed to the setting input C of a further flip-flop 70 which then emits the time comparison signal S23 at its output Q until reset by the resetting signal S41.

A D-flip-flop 71 serves as an arrival time detector 22; the time comparison signal S23 is fed to its preparator input D and the zero passage signal S21 is fed to its stage input C. The leading edge of the two signals thereby serve as time measuring points. Depending on the phase position of these two leading edges, an early measured signal S24 occurs at the output Q or the late measured signal S25 occurs at the output Q̄.

The early tracking signal S16 is fed through an inverter 72 and the late tracking signal S17 through an inverter 73 to a respective incandescent diode 74 or 75, which have a common, current limiting resistor 76. When the arrival delay signal S14 tracks the trailing edge of an impulse of the rectangular signal S12, as is desired, the diodes 74 and 75 light up alternately.

FIGS. 3 and 4 show various signals with respect to time. When the transmission signal S43 (first line) is emitted, the transducer 3 produces an ultrasonic signal S3 which, after a transit time $t_z$, is sensed by the transducer 4 and received as an electric ultrasonic signal S8. Simultaneously with emission of the transmission signal S43, the counter 39 starts to count the impulses S38 delivered by the oscillator 37. After 256 or some other predetermined number of impulses, the reference signal S40 is delivered. This corresponds to an expected transit time $t_e$ which decreases with rising frequency of the pulse train S38 and increases with falling frequency. The expected transit time $t_e$ is delayed until after the actual transit time $t_z$ in the regulating circuit of the apparatus so that the sonic velocity and flow velocity are accurately formed by the main signal S27 and auxiliary signal S31, respectively. It will also be evident that the ultrasonic signal S8 starts with a smaller amplitude, for which reason the initial portion of the signal is not particularly useful for determining the actual transit time $t_z$.

FIG. 4 first of all shows an enlarged representation of the ultrasonic signal S8. By means of rectification one obtains the rectified signal S54 and by smoothing one obtains the enveloping curve S49. In addition, amplification and clipping of the ultrasonic signal S8 results in the rectangular signal S12.

The envelope curve S49 produces the output signal S56 in the ramp amplifier 55. This signal is compared with the constant threshold value S58. As soon as the threshold value has been reached, the flip-flop 60 is triggered and emits the arrival delay signal S14. The regulation carried out by the phase detector 15 and the regulating means 18 ensures that the arrival delay time $t_a$ that is thus determined finishes at the instant at which zero passage a occurs with the trailing edge of the rectangular signal S12. If it is determined in the phase detector 15 that the arrival delay time $t_a$ is too short, the output signal S56 is displaced downwardly with the aid of the control voltage S19, whereby the delay time $t_a$ is increased. If the delay time $t_a$ is too long, the output signal S56 is raised, whereby the delay time is shortened. The next following positive-going zero crossover b of the rectangular signal S12 is determined in the zero crossover selector means 20 which generates the zero crossover signal S21. With a finally regulated arrival delay time $t_a$, this occurs precisely half a period p/2 of the ultrasonic signal 8 after occurrence of the arrival delay signal S14. One thereby obtains a precisely defined delay time, even if commencement of the signal of the ultrasonic signal S8 cannot be very accurately determined.

The reference signal S40 is emitted at the expected instant of arrival which, in the regulated condition, coincides with the actual instant of arrival. With the aid of the reference delay signal S69, a reference delay time $t_b$ is added in the reference delay means 44 and at the end of this the time comparison signal S23 appears. The leading edge of the zero crossover signal S21 is compared in phase with the leading edge of this time comparison signal S23 and appropriately evaluated as being early or late with respect thereto such that the time positions of the reference pulse may be adjusted to track the zero crossover point.

The voltage controlled oscillator 37 may be of conventional design or alternatively may be an integrated circuit chip such as the ICL 8038. The frequency divider 39 may also be of conventional design or alternatively may be a series of discrete logic components such as integrated circuits 7474. The element 46 may be a bistable element such as a flip-flop. The summing circuit 32 may be an operational amplifier such as a 301A with the input switching circuitry 33 being an integrated circuit elements CA 4016. The remaining circuit elements are all described in greater detail in FIG. 2 and may be operational amplifiers. In particular, the amplifier 47 may be an integrated circuit component MC 1590, the amplifier 11 may be an integrated circuit such as MC 1414L, the amplifier 50 may be an integrated circuit such as 301A, the differential ramp circuit 55 may be the integrated circuit HA 2605, and the threshold detector 57 may be an integrated circuit MC 1414L, while the elements 60, 61, 65, and 71 may be logic elements of the 7400 series. The NAND gates 62 and 63 may in like manner be of the 7400 series, whereas the amplifier 64 may be 301A, the monostable vibrator 68 may be of the 7400 series and the flip-flop 70 may be of the 7400 series.

I claim:

1. Apparatus for ascertaining the time of arrival of an alternating signal comprising:
   arrival delay means responsive to the commencement of said signal for generating an arrival delay signal,
   a zero crossover detector responsive to the zero crossing of said alternating signal in a first sense after said delay signal for generating a time signal corresponding to said time of arrival,
   timing means for generating a reference signal corresponding to the expected time of arrival of said alternating signal, and
   a time of arrival detector responsive to said reference signal and to said time signal for ascertaining said time of arrival and controlling said timing means in accordance therewith,
   regulating means responsive to said arrival delay signal and to the preceding zero crossing of said alternating signal in a second sense opposite said sense for adjusting the timing of said arrival delay signal to correlate in time with said second sense zero crossing, whereby said arrival delay signal always immediately precedes said first sense zero crossing.

2. Apparatus according to claim 1 wherein said regulating means also varies the timing of said reference signal in the same sense as the arrival delay signal.

3. Apparatus according to claim 2 wherein said regulating means includes a phase detector which compares the phase of said arrival delay signal with that of said second sense zero crossings to provide early signals in one polarity when the arrival delay signal arrives too early and late signals of another polarity opposite said one polarity when the arrival delay signal arrives too late, and an integrator responsive to said early and late signals for providing a control signal for adjusting said arrival delay signal timing.

4. Apparatus according to claim 3 wherein said reference delay means includes a monostable multi-vibrator adapted to be triggered by said reference signal and which includes a RC element which controls its trigger, and said control means being connected to vary the charging voltage of said RC element thereby to vary said trigger.

5. Apparatus according to claim 1 wherein said regulating means includes a phase detector which compares the phase of said arrival delay signal with that of said second sense zero crossings to provide early signals in one polarity when the arrival delay signal arrives too early and late signals of another polarity opposite said one polarity when the arrival delay signal arrives too late, and an integrator responsive to said early and late signals for providing a control signal for adjusting said arrival delay signal timing.

6. The apparatus according to claim 5 which also includes means for rectifying the received alternating signal, means for converting the rectified signal into a substantially linear rising signal,
a threshold detector for ascertaining when said rising signal achieves a predetermined threshold value thereby to generate said arrival delay signal.

7. The apparatus according to claim 6 wherein said phase detector comprises a D-flip-flop having a preparatory input connected to receive said alternating signals and a stage input connected to received said arrival delay signal, said flip-flop having one output adapted to provide said early signals and other output connected to provide said late signals.

8. Apparatus according to claim 7 which includes a differential amplifier having one input connected to receive said control input voltage control signal and the other output connected to receive said envelope signal thereby to provide said linear rising signal.

9. Apparatus according to claim 6 wherein said zero crossover detected comprises a D-flip-flop which is resettable after each measurement, and includes a preparatory input connected to receive said arrival delay signal and a stage input connected to receive said alternating signals and output adapted to provide for generating said time signals.

10. Apparatus according to claim 9 which includes a second flip-flop connected to receive said arrival delay signal and to store the same, said flip-flop being resettable after each measurement.

11. Apparatus according to claim 10 wherein said zero crossover detector includes a D-flip-flop which is resettable after each measurement, and has a preparatory input connected to receive said arrival delay signal and a stage input connected to receive said alternating signals and an output for providing said time signal.

12. Apparatus according to claim 10 wherein said time of arrival detector includes a D-flip-flop having a preparatory input connected to receive said delay reference signal in a stage input connected to receive said time signal and a pair of output adapted to provide said early signal at one output and a late signal at its other output depending on whether the time signal occurs before or after said delay reference signal.

13. Apparatus according to claim 10 which also includes an indicating means comprising two incandescent diodes each energized by an inverter controlled by the early or late signals respectively.

14. Apparatus for ascertaining the time of arrival of an alternating signal comprising:
arrival delay means responsive to the commencement of said signal for generating an arrival delay signal,
a zero crossover detector responsive to the zero crossing of said alternating signal in a first sense afte said delay signal for generating a time signal,
timing means for generating a reference signal corresponding to the expected time of arrival of said alternating signal, and
a time of arrival detector responsive to said reference signal and to said time signal for ascertaining said time of arrival and controlling said timing means in accordance therewith,
regulating means responsive to said arrival delay signal and to the preceding zero crossing of said alternating signal in a second sense opposite said first sense for adjusting the timing of said reference signal to correlate in time with said first sense zero crossing.

15. Apparatus for ascertaining the time of arrival of an alternating signal comprising:
arrival delay means responsive to the commencement of said signal for generating and arrival delay signal,
a zero crossover detector responsive to the zero crossing of said alternating signal in a first sense after said delay signal for generating a time signal corresponding to said time of arrival,
regulating means responsive to said arrival delay signal and to the preceding zero crossing of said alternating signal in a second sense opposite said first sense for adjusting the timing of said arrival delay signal to correlate in time with said second sense zero crossing, whereby said arrival delay signal always immediately precedes said first sense zero crossing.

* * * * *